(12) United States Patent
Liu (10) Patent No.: US 9,968,134 B2
(45) Date of Patent: May 15, 2018

(54) ATOMIZER AND ELECTRONIC CIGARETTE

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 677 days.

(21) Appl. No.: 14/504,276

(22) Filed: Oct. 1, 2014

(65) Prior Publication Data
US 2015/0282528 A1    Oct. 8, 2015

Related U.S. Application Data (63) Continuation of application No. PCT/CN2014/074932, filed on Apr. 8, 2014.

(51) Int. Cl.
*A24F 47/00* (2006.01)
*A61M 15/06* (2006.01)

(52) U.S. Cl.
CPC .......... *A24F 47/008* (2013.01); *A61M 15/06* (2013.01)

(58) Field of Classification Search
CPC .... A24F 47/008; A24F 47/0002; A26M 15/06
See application file for complete search history.

(56) References Cited

U.S. PATENT DOCUMENTS

2011/0303231 A1\* 12/2011 Li .................. A24F 47/008
                                                  131/329
2013/0160765 A1    6/2013 Liu

FOREIGN PATENT DOCUMENTS

| CN | 203087526 U | 7/2013 |
| CN | 203168034 U | 9/2013 |
| CN | 103504478 A | 1/2014 |
| CN | 203388273 U | 1/2014 |
| CN | 103504478 A | 2/2014 |
| CN | 203633513   | 6/2014 |

OTHER PUBLICATIONS

International Search Report issued by the State Intellectual Property Office of the P.R. China for Application No. PCT/CN2014/074932, dated Jul. 29, 2014.

\* cited by examiner

*Primary Examiner* — Anthony Calandra
(74) *Attorney, Agent, or Firm* — Tim Tingkang Xia, Esq.; Locke Lord LLP (57) ABSTRACT

An atomizer and an electronic cigarette are provided. The atomizer comprises a sleeve and an atomizing core. A suction nozzle is formed on an end portion of the sleeve; a tobacco-tar storage chamber and an accommodating chamber are defined in the sleeve; an end portion of the sleeve far away from the suction nozzle is an opening end with a tobacco-tar filler hole. The atomizing core includes an atomizing sleeve, an electrode assembly, a heating wire assembly and a tobacco-tar latch member; a tobacco-tar inlet is defined in an end portion of the atomizing sleeve far away from the suction nozzle; the tobacco-tar latch member is sheathed in the atomizing sleeve; the tobacco-tar inlet and the heating wire assembly are respectively arranged on two opposite end portions or two opposite side portions of the tobacco-tar latch member. The present disclosure effectively protects users from tasting the tobacco tar without atomization.

18 Claims, 6 Drawing Sheets

ATOMIZER AND ELECTRONIC CIGARETTE

CROSS-REFERENCE TO RELATED APPLICATION

This application is a continuation application of International Patent Application No. PCT/CN2014/074932, by Qiuming LIU, filed Apr. 8, 2014, which is hereby incorporated herein in its entirety by reference.

FIELD OF THE INVENTION

The present disclosure relates to the field of daily electrical products, and more particularly relates to an atomizer and an electronic cigarette.

BACKGROUND OF THE INVENTION

A conventional electronic cigarette comprises an atomizer and a battery assembly supplying electric power to the atomizer. When the atomizer is working, the atomizer atomizes tobacco tar stored in the atomizer to generate smoke for users to taste.

Figure 1:
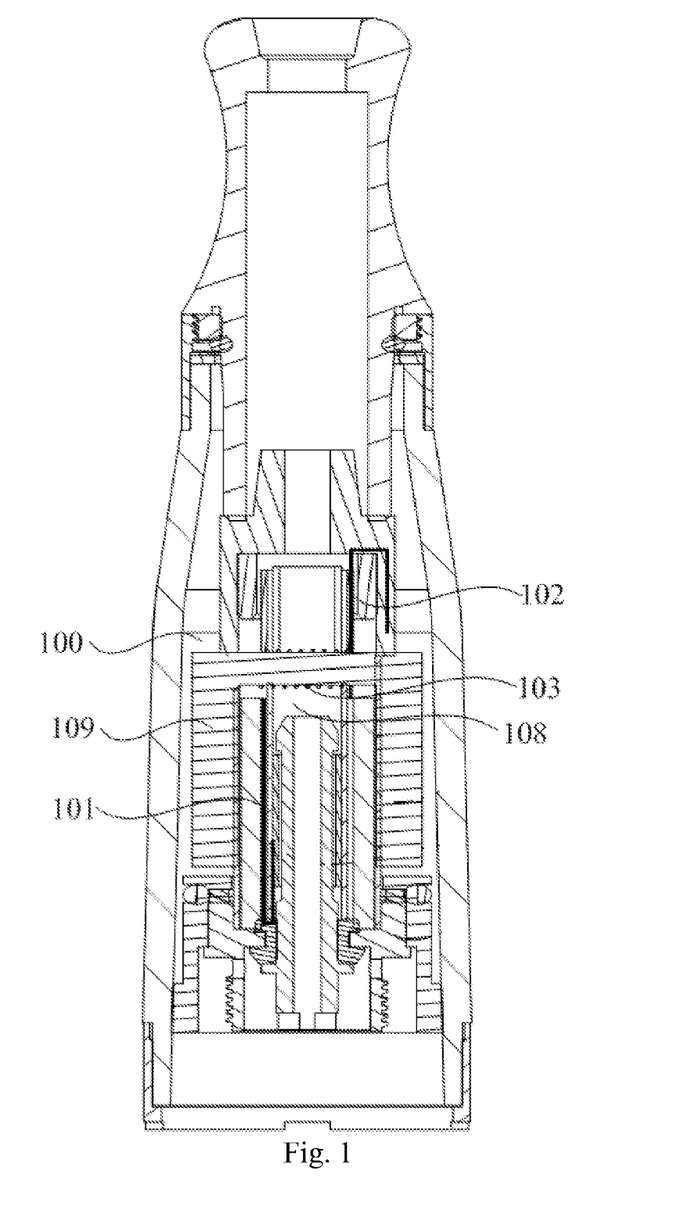
FIG. 1 is an inner structural schematic view of a conventional atomizer.

As shown in FIG. 1, the atomizer usually includes a tobacco-tar storage chamber 100, a first electrode connection member 101 and a second electrode connection member 102; the first electrode connection member 101 and the second electrode connection member 102 are respectively connected to the battery assembly electrically. Moreover, the first electrode connection member 101 and the second electrode connection member 102 are respectively connected with two terminals of a heating wire 103, and extend towards two terminals of the heating wire 103 respectively. The heating wire 103 is mounted in a smoke flowing channel 108 of the atomizer; a tobacco-tar outlet (not labeled) is defined in the tobacco-tar storage chamber 100; the heating wire 103 is wound on a tobacco-tar guiding rope 109 passing through the tobacco-tar outlet and extending into the tobacco-tar storage chamber 100, and the tobacco-tar outlet is disposed corresponding to the heating wire 103. In the structure of the atomizer, the uncontrollable flow of tobacco tar from the tobacco-tar guiding rope 109 to the heating wire 103 easily results in a overflow of tobacco tar reaching the heating wire 103, and without a timely atomization of the heating wire 103, the tobacco tar flows into the smoke flowing channel 108 consequently. In addition, the tobacco tar left in the tobacco-tar outlet easily permeates into the smoke flowing channel 108 and further flows out from the smoke flowing channel 10, resulting in leakage of the tobacco tar, thus causing a taste of the tobacco tar to the smoker.

SUMMARY OF THE INVENTION

The objective of the present disclosure is to provide an atomizer and an electronic cigarette which can avoid the leakage of the tobacco tar beside the heating wire, substantially is shown in and/or described in connection with at least one of the figures, as set forth more completely in the claims, aiming at the drawbacks of the tobacco tar easily leaks out besides the heating wire of the aforementioned atomizer.

The technical solutions of the present disclosure for solving the technical problems are as follows:

In one aspect, an atomizer configured for assembling with a battery assembly to form an electronic cigarette and comprising a sleeve and an atomizing core is provided with a suction nozzle formed on an end portion of the sleeve, and a smoke outlet defined in an end portion of the suction nozzle; wherein, a tobacco-tar storage chamber configured for accommodating tobacco tar and an accommodating chamber configured for accommodating the atomizing core are defined in the sleeve; an end portion of the sleeve far away from the suction nozzle is configured as an opening end; a tobacco-tar filler hole communicating with the tobacco-tar storage chamber and the accommodating chamber is defined in the opening end; and the atomizing core is detachably mounted in the sleeve and completely covers the tobacco-tar filler hole;

the atomizing core includes an atomizing sleeve inserted in the accommodating chamber, an electrode assembly inserted into an end portion of the atomizing sleeve and configured for electrically connecting with the battery assembly, a heating wire assembly accommodated in the atomizing sleeve and electrically connecting with the electrode assembly, and a tobacco-tar latch member made of oil absorption material and configured for transmitting the tobacco tar to the heating wire assembly to atomize; a tobacco-tar inlet communicating with the tobacco-tar storage chamber is defined in an end portion of the atomizing sleeve far away from the suction nozzle; the tobacco-tar latch member is sheathed in the atomizing sleeve; the tobacco-tar inlet and the heating wire assembly are respectively arranged on two opposite end portions or two opposite side portions of the tobacco-tar latch member.

In one embodiment, the electrode assembly includes an external electrode and an internal electrode, and the external electrode and the internal electrode are respectively configured for electrically connecting with the battery assembly; an outer portion of the internal electrode is sheathed in the external electrode; the atomizing sleeve is inserted in the external electrode; a hollow air pipe is connected to an end portion of the internal electrode abutting the suction nozzle; the heating wire assembly is mounted in the air pipe; the tobacco-tar latch member is resisted between the atomizing sleeve and the air pipe;

an air inlet communicating with an outside of the atomizer is defined in the internal electrode; the air inlet, the air pipe and the smoke outlet are connected in sequence.

In another embodiment, the tobacco-tar latch member is a wool pipe coaxial with the atomizing sleeve; an outer surface of the wool pipe abuts against an inner surface of the atomizing sleeve.

In another embodiment, the sleeve includes a sleeve body and a stepped hole defined in the sleeve body; the stepped hole includes a counterbore portion and a through-hole portion communicating with the smoke outlet; the atomizer further comprises a hollow tobacco-tar blocked pipe mounted on a bottom surface in the counterbore portion; an inner surface in the counterbore portion and an outer surface of the tobacco-tar blocked pipe cooperatively form the tobacco-tar storage chamber; an inner surface of the tobacco-tar blocked pipe forms the accommodating chamber.

In another embodiment, the atomizer further comprises a one-way valve configured for turning on or cutting off communication between the smoke outlet and the through-hole portion; when air flow flows from the through-hole portion to the smoke outlet, the one-way valve turns on the communication between the smoke outlet and the through-hole portion; when air flow flows from the smoke outlet to the through-hole portion, the one-way valve cuts off the communication between the smoke outlet and the through-hole portion.

In another embodiment, the one-way valve is mounted in the through-hole portion; an outer surface of the one-way valve is sheathed in the tobacco-tar blocked pipe.

In another embodiment, the sleeve is integrated with the suction nozzle.

In another embodiment, a sealing ring is mounted between the electrode assembly and the tobacco-tar filler hole.

In another embodiment, a bottom surface in the counterbore portion extends towards a side far away from the suction nozzle to form a limiting part; an end portion of the tobacco-tar blocked pipe is inserted in the limiting part.

In another embodiment, the atomizer further comprises a sealing member is hermetically mounted between the atomizing core and the one-way valve.

In another aspect, an electronic cigarette comprising an atomizer and a battery assembly connecting with the atomizer is provided; the atomizer comprise a sleeve and an atomizing core is provided with a suction nozzle formed on an end portion of the sleeve, and a smoke outlet defined in an end portion of the suction nozzle; wherein, a tobacco-tar storage chamber configured for accommodating tobacco tar and an accommodating chamber configured for accommodating the atomizing core are defined in the sleeve; an end portion of the sleeve far away from the suction nozzle is configured as an opening end; a tobacco-tar filler hole communicating with the tobacco-tar storage chamber and the accommodating chamber is defined in the opening end; and the atomizing core is detachably mounted in the sleeve and completely covers the tobacco-tar filler hole;

the atomizing core includes an atomizing sleeve inserted in the accommodating chamber, an electrode assembly inserted into an end portion of the atomizing sleeve and configured for electrically connecting with the battery assembly, a heating wire assembly accommodated in the atomizing sleeve and electrically connecting with the electrode assembly, and a tobacco-tar latch member made of oil absorption material and configured for transmitting the tobacco tar to the heating wire assembly to atomize; a tobacco-tar inlet communicating with the tobacco-tar storage chamber is defined in an end portion of the atomizing sleeve far away from the suction nozzle; the tobacco-tar latch member is sheathed in the atomizing sleeve; the tobacco-tar inlet and the heating wire assembly are respectively arranged on two opposite end portions or two opposite side portions of the tobacco-tar latch member.

In one embodiment, the electrode assembly includes an external electrode and an internal electrode, and the external electrode and the internal electrode are respectively configured for electrically connecting with the battery assembly; an outer portion of the internal electrode is sheathed in the external electrode; the atomizing sleeve is inserted in the external electrode; a hollow air pipe is connected to an end portion of the internal electrode abutting the suction nozzle; the heating wire assembly is mounted in the air pipe; the tobacco-tar latch member is resisted between the atomizing sleeve and the air pipe;

an air inlet communicating with an outside of the atomizer is defined in the internal electrode; the air inlet, the air pipe and the smoke outlet are connected in sequence.

In another embodiment, the tobacco-tar latch member is a wool pipe coaxial with the atomizing sleeve; an outer surface of the wool pipe abuts against an inner surface of the atomizing sleeve.

In another embodiment, the sleeve includes a sleeve body and a stepped hole defined in the sleeve body; the stepped hole includes a counterbore portion and a through-hole portion communicating with the smoke outlet; the atomizer further comprises a hollow tobacco-tar blocked pipe mounted on a bottom surface in the counterbore portion; an inner surface in the counterbore portion and an outer surface of the tobacco-tar blocked pipe cooperatively form the tobacco-tar storage chamber; an inner surface of the tobacco-tar blocked pipe forms the accommodating chamber.

In another embodiment, the atomizer further comprises a one-way valve configured for turning on or cutting off communication between the smoke outlet and the through-hole portion; when air flow flows from the through-hole portion to the smoke outlet, the one-way valve turns on the communication between the smoke outlet and the through-hole portion; when air flow flows from the smoke outlet to the through-hole portion, the one-way valve cuts off the communication between the smoke outlet and the through-hole portion.

In another embodiment, the one-way valve is mounted in the through-hole portion; an outer surface of the one-way valve is sheathed in the tobacco-tar blocked pipe.

In another embodiment, the sleeve is integrated with the suction nozzle.

In another embodiment, a sealing ring is mounted between the electrode assembly and the tobacco-tar filler hole.

In another embodiment, a bottom surface in the counterbore portion extends towards a side far away from the suction nozzle to form a limiting part; an end portion of the tobacco-tar blocked pipe is inserted in the limiting part.

In another embodiment, the atomizer further comprises a sealing member is hermetically mounted between the atomizing core and the one-way valve.

When implementing the atomizer and the electronic cigarette of the present disclosure, the following advantageous effects can be achieved:

1. The atomizer is provided with a structure that the tobacco-tar inlet and the heating wire assembly are respectively arranged on two opposite end portions or two opposite side portions of the tobacco-tar latch member, and thus the tobacco tar in the tobacco-tar storage chamber would be transmitted to the heating wire assembly through the tobacco-tar latch member, in which case, it would not cause overflow of tobacco tar flowing to the heating wire assembly, so as to efficiently avoid the smoker's tasting of the tobacco tar without atomization because of the lack of timely atomizing. The tobacco-tar latch member can have a function of transmitting the tobacco tar, as well as preventing the tobacco tar from permeating into the smoke flowing channel, so as to prevent a smoker from tasting the tobacco tar without atomization, thus guaranteeing a good user experience.

2. With The atomizer's structure of the one-way valve, the smoke can be prevented to flowing back to the atomizer or even flowing into the battery assembly through the atomizer during operation, and thus effectively avoid circuits in the battery assembly being damaged by contamination of the tobacco tar.

3. As the heating wire assembly is mounted on an end portion of the air pipe far away from the electrode assembly, during operation, the distance of the smoke generated by atomizing the tobacco tar flowing out from the smoke outlet is short, it can avoid a smoker tasting condensed tobacco tar generated effectively, further improving a user comfort level.

4. As the tobacco-tar filler hole is defined in an end portion of the sleeve far away from the suction nozzle, in the case of adding or replacing tobacco tar in the atomizer or replaced, just the atomizing core would be disassembled from the sleeve, the tobacco-tar filler hole be turned up, and the tobacco tar can be injected into the tobacco-tar storage chamber through the tobacco-tar filler hole. With this structure, adding or replacing the tobacco tar can be convenient. Compared with adding or replacing the tobacco tar through an end portion of the suction nozzle in prior art, the method of adding or replacing the tobacco tar of the present disclosure can avoid contaminating the suction nozzle, and thus the use health level of the atomizer can be improved.

5. The atomizing core is replaceable so that maintenance cost of the atomizer can be reduced.

BRIEF DESCRIPTION OF THE DRAWINGS

The present disclosure will be further described with reference to the accompanying drawings and embodiments in the following. In the accompanying drawings.

DETAILED DESCRIPTION OF THE PREFERRED EMBODIMENT

So as to further clearly explain the technique character, the object and the effect, a specific implement of the present invention will be illustrated in detail with references to the accompanying drawings.

Figure 2:
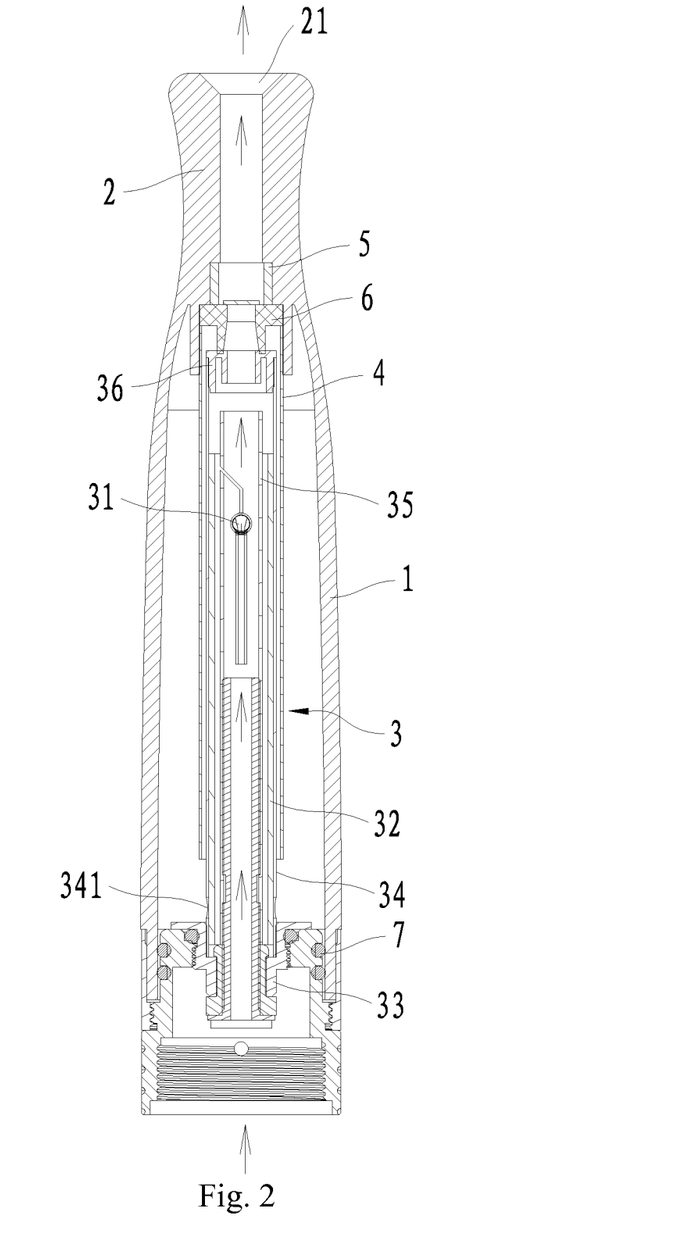
FIG. 2 is an inner structural schematic view of an atomizer of a first preferred embodiment of the present disclosure.

As shown in FIG. 2, according to a first preferred embodiment of the present disclosure, an atomizer is provided for assembling with a battery assembly (not labeled) to form an electronic cigarette. The atomizer comprises a sleeve 1, a suction nozzle 2, an atomizing core 3, a tobacco-tar blocked pipe 4, a one-way valve 5, a sealing member 6 and a sealing ring 7.

Figure 3:
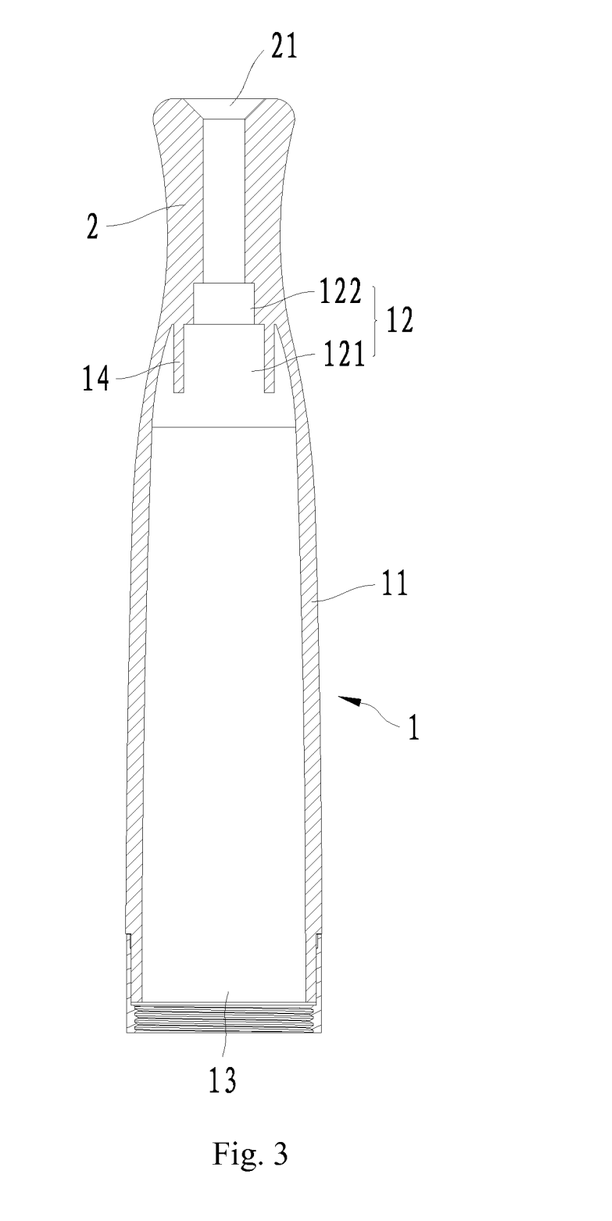
FIG. 3 is a structural view of a sleeve and a suction nozzle of the atomizer shown in FIG. 2.
Figure 5:
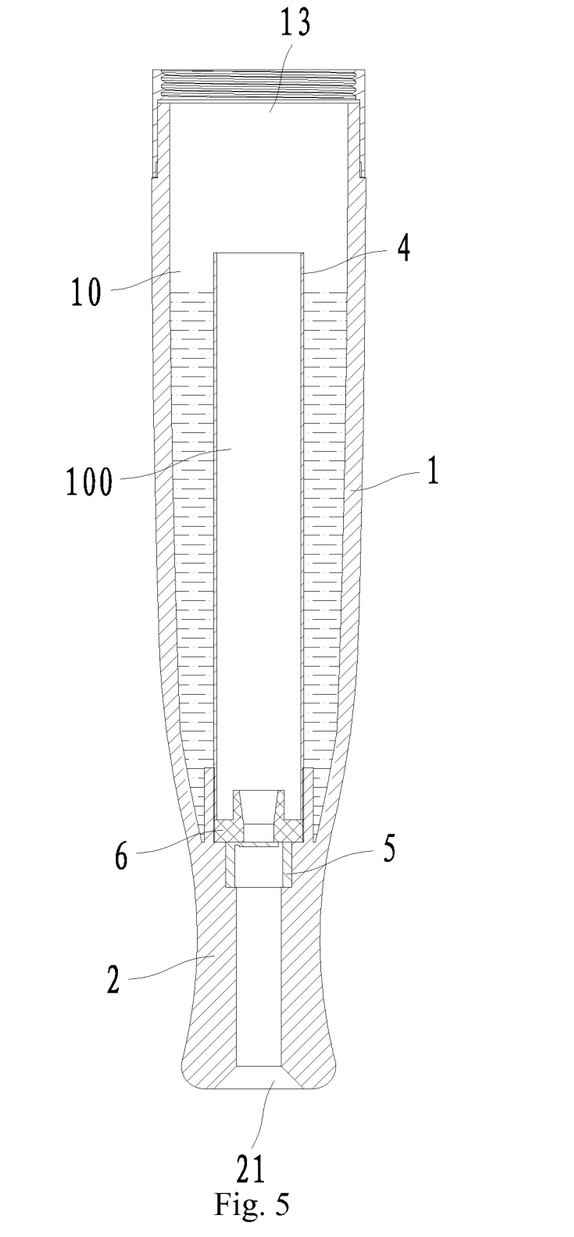
FIG. 5 is a schematic view of adding tobacco tar into the sleeve of the atomizer shown in FIG. 2.

Specifically, as shown in FIG. 3, FIG. 5 and FIG. 2, the sleeve 1 includes a tobacco-tar storage chamber 10 for accommodating tobacco tar and an accommodating chamber 100 for accommodating the atomizing core 3. The suction nozzle 2 is formed at an end portion of the sleeve 1, and an end portion of the sleeve 1 far away from the suction nozzle 2 is an opening end. Herein, a tobacco-tar filler hole 13 communicating with the tobacco-tar storage chamber 10 and the accommodating chamber 100 is defined in the opening end. In this embodiment, the sleeve 1 includes a sleeve body 11, a stepped hole 12 and a limiting part 14. The sleeve body 11 is approximately hollow, and the stepped hole 12 is defined in the sleeve body 11. The stepped hole 12 includes a counterbore portion 121 and a through-hole portion 122, and the counterbore portion 121 and the through-hole portion 122 communicate with each other. The tobacco-tar filler hole 13 is an opening of an end portion of the counterbore portion 121 far away from the through-hole portion 122, and through the tobacco-tar filler hole 13, adding or replacing tobacco tar into the atomizer. The tobacco-tar blocked pipe 4 is hollow and mounted on a bottom surface in the counterbore portion 121. The tobacco-tar blocked pipe 4 can be integrated with or detachably connected with the sleeve 1, which is not limited here. The tobacco-tar storage chamber 10 is formed by the inner surface of the counterbore portion 121 and the outer surface of the tobacco-tar blocked pipe 4, and the accommodating chamber 100 is formed by the inner surface of the tobacco-tar blocked pipe 4. The through-hole portion 122 and a smoke outlet 21 communicate with each other, and cooperatively form a channel configured for smoke to flow. The atomizing core 3 is detachably mounted in the sleeve 1 and can be configured for completely fitting and sealing the tobacco-tar filler hole 13. The limiting part 14 is configured for assembling the tobacco-tar blocked pipe 4, and the limiting part 14 is approximately a hollow cylindrical structure, and integrated with the sleeve body 11. In this embodiment, the limiting part 14 is formed by a bottom surface in the counterbore portion 121 extending towards a side far away from the suction nozzle 2; an inner surface of the limiting part 14 and an outer surface of the tobacco-tar blocked pipe 4 are resisted with each other. When inserted in the limiting part 14, the tobacco-tar blocked pipe 4, the tobacco-tar blocked pipe 4 communicates with the through-hole portion 122. With the limiting part 14, it is convenient for the assembly location of the tobacco-tar blocked pipe 4 during assembling, so as to improve assembly efficiency. In another embodiment of the present disclosure, the limiting part 14 can also be detachably mounted on a bottom surface in the counterbore portion 121.

As shown in FIG. 5 and FIG. 3, in the case of tobacco tar adding or replacing in the atomizer or, the atomizing core 3 would be disassembled from the sleeve 1 at first, the tobacco-tar filler hole 13 should be turned up, and then the tobacco tar can be injected into the tobacco-tar storage chamber 10 through the tobacco-tar filler hole 13. That is, the tobacco tar is injected into the space between the inner surface of the counterbore portion 121 and the outer surface of the tobacco-tar blocked pipe 4. After the injection of the tobacco tar is completed, the atomizing core 3 should be inserted into the accommodating chamber 100 and the atomizing core 3 can completely fit to seal the tobacco-tar filler hole 13, in which case the atomizer can work normally.

As shown in FIG. 3, the suction nozzle 2 is provided with an arc structure, and the suction nozzle 2 can be round or coned, etc. The texture and shape of the suction nozzle 2 should be fit for a user's mouth, and the suction nozzle 2 is made of soft plastic material or wood material. A smoke outlet 21 is defined in an end portion of the suction nozzle 2, and the smoke outlet 21 is defined on an end portion of the suction nozzle 2 far away from the atomizing core 3. In this embodiment, the suction nozzle 2 is integrated with the sleeve 1 to improve the integral effect of the atomizer. In any other embodiments of the present disclosure, the suction nozzle 2 can be detachably connected to the sleeve 1. With this structure, it is convenient for cleaning the suction nozzle 2, and improves health level of using the atomizer.

Figure 4:
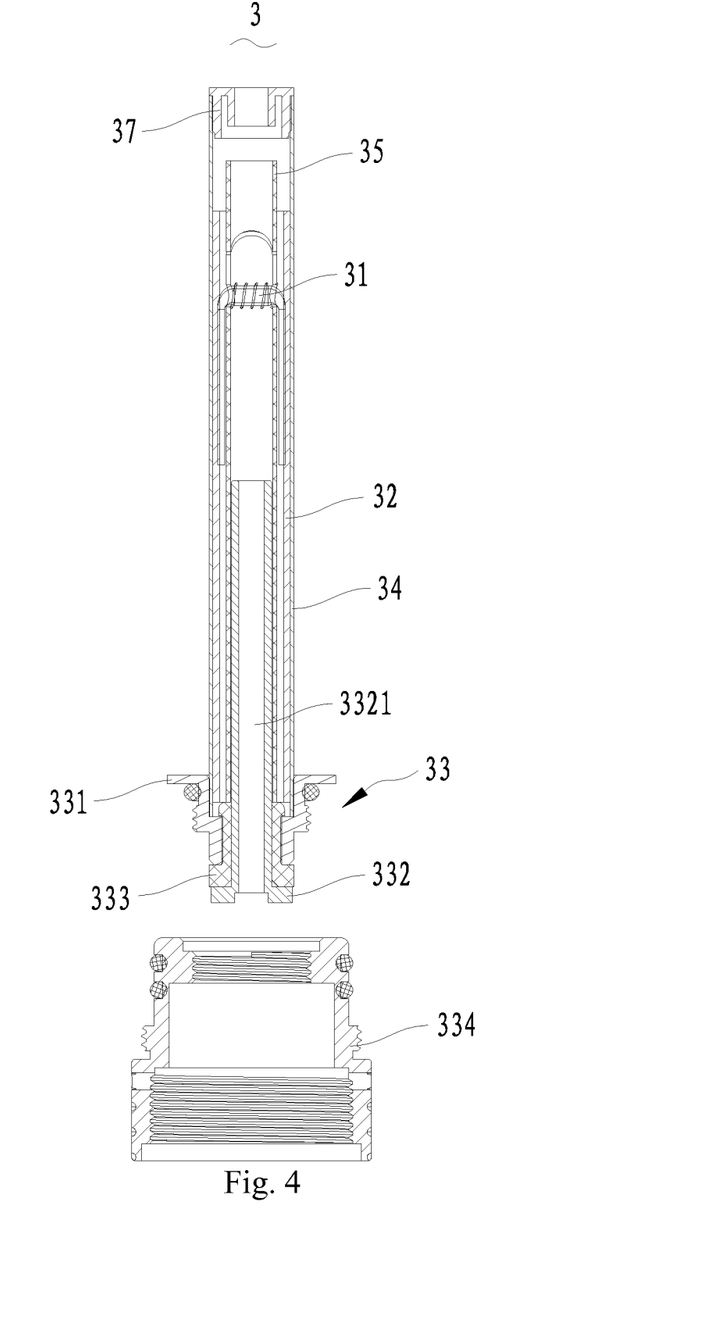
FIG. 4 is a structural view of an atomizing core of the atomizer shown in FIG. 2.

As shown in FIG. 4 and FIG. 3, the atomizing core 3 is configured for atomizing the tobacco tar stored in the tobacco-tar storage chamber 10. The atomizing core 3 is detachably mounted on the sleeve 1 and can completely fit and seal the tobacco-tar filler hole 13 of the tobacco-tar storage chamber 10. During operation, the atomizing core 3 can be replaced conveniently, thus reducing maintenance cost of the atomizer. Specifically, the atomizing core 3 includes a heating wire assembly 31, a tobacco-tar latch member 32, an electrode assembly 33, an atomizing sleeve 34, an air pipe 35 and an end cover 36.

The heating wire assembly 31 is configured for atomizing the tobacco tar stored in the tobacco-tar storage chamber 10. The heating wire assembly 31 is electrically connected to the electrode assembly 33. The heating wire assembly 31 includes a glass filament (not labeled) and a heating wire (not labeled). Two terminals of the glass filament respectively abut against the tobacco-tar latch member 32 to absorb the tobacco tar stored in the tobacco-tar latch member 32. The heating wire is intertwined with the glass filament, and two terminals of the heating wire are respectively connected to the electrode assembly 33 electrically. When electrified, the heating wire can atomize the tobacco tar absorbed in the glass filament to generate smoke for a smoker to taste. In this embodiment, the glass filament is approximately U-shaped, and the glass filament horizontally runs through the air pipe 35, that is, two opposite mounting holes (not labeled) are defined in the lateral surface of the air pipe 35; the two terminals of the glass filament are respectively mounted in the two mounting holes. The heating wire is intertwined with the glass filament located in the air pipe 35, so that the smoke generated by the atomizing core 3 can flow out of the air pipe 35. In this embodiment, the heating wire assembly 31 is mounted on an end portion of the air pipe 35 far away from the electrode assembly 33. During operation, the distance of the smoke generated by atomizing the tobacco tar flowing out from the suction nozzle 2 is short, and condensation of the smoke can be avoided effectively, which improves the comfort level of users. Of course, the material, shape and structure of the heating wire assembly 31 is not limited herein.

The tobacco-tar latch member 32 is configured for absorbing the tobacco tar in the tobacco-tar storage chamber 10 and transmitting the tobacco tar to the heating wire assembly 31. The tobacco-tar latch member 32 is made of oil absorption material. The oil absorption material can be conventional oil absorption cotton or oil absorption fibers, etc. In this embodiment, the tobacco-tar latch member 32 is a wool pipe coaxial with the atomizing sleeve 34; outer surfaces of the air pipe 35 is sheathed in the tobacco-tar latch member 32, and abuts against the two terminals of the glass filament. The structure of the tobacco-tar latch member 32 has a function of transmitting the tobacco tar, as well as preventing the tobacco tar from permeating into the air pipe 34, thus preventing a smoker from tasting the tobacco tar without atomization, and guaranteeing a good user experience.

The electrode assembly 33 is configured for achieving electrical connection between the heating wire assembly 31 and the battery assembly, as well as for completely fitting and sealing the tobacco-tar filler hole 13 of the tobacco-tar storage chamber 10. In this embodiment, the electrode assembly 33 includes an external electrode 331, an internal electrode 332, an insulating member 333 and a connecting member 334, wherein the external electrode 331 and the internal electrode 332 are respectively configured for electrically connecting with the battery assembly. The external electrode 331 is approximately configured of a stepladder cylindrical structure, and sheaths an outer portion of the internal electrode 332. The internal electrode 332 is approximately a cylindrical structure, with an air inlet 3321 defined in the axial direction. The air inlet 3321 communicates with an outside of the atomizer, that is, air outside the atomizer can enter into the atomizing core 3 through the air inlet 3321. The air inlet 3321, the air pipe 35 and the smoke outlet 21 are connected in sequence to form a channel for air flow to flow. The insulating member 333 is configured for achieving insulation between the external electrode 331 and the internal electrode 332. The insulating member 333 is approximately of a hollow cylindrical structure, and is sleeved between the external electrode 331 and the internal electrode 332.

The connecting member 334 is approximately configured of a hollow cylindrical structure, and is made of conductive material. The connecting member 334 sheaths an outer surface of the external electrode 331 to achieve electrical connection with the external electrode 331. Moreover, an outer surface of the connecting member 334 is connected to an inner surface of the sleeve 1. In this embodiment, a first external thread is defined on the outer surface of the connecting member 334, correspondingly, a first internal thread corresponding to the first external thread is defined on an inner surface of an end portion of the sleeve body 11 far away from the suction nozzle 2, and the atomizing core 3 is detachably mounted on the sleeve 1 through the first external thread of the connecting member 334. A second internal thread corresponding to the battery assembly is defined on an inner surface of an end portion of the connecting member 334 far away from the external electrode 331. The atomizer connects with the battery assembly through the second internal thread. In this embodiment, the internal electrode 332 is sheathed in the insulating member 333, the insulating member 333 is sheathed in the external electrode 331, and the external electrode 331 is sheathed in the connecting member 334. When the connecting member 334 is mounted on the sleeve 1, the electrode assembly 33 seals a tobacco-tar filled hole 13 of the tobacco-tar storage chamber 10. In another embodiment of the present disclosure, the connecting member 334 is integrated with the external electrode 331, so that it is more convenient to assemble the electrode assembly 33.

The atomizing sleeve 34 is a hollow cylindrical structure, with two openings respectively defined in two opposite end portions. The atomizing sleeve 34 is mounted on an end portion of the external electrode 331 abutting the tobacco-tar storage chamber 10. In this embodiment, the atomizing sleeve 34 sheaths an outer surface of an end portion of the external electrode 331 abutting the tobacco-tar storage chamber 10. A tobacco-tar inlet 341 communicating with the tobacco-tar storage chamber 10 is defined in a lateral surface of the atomizing sleeve 34. A plurality of tobacco-tar inlet(s) 341 can be defined, and uniformly distributed in the lateral surface of the atomizing sleeve 34. The tobacco-tar latch member 32 is mounted in the atomizing sleeve 34, and the outer surface of the tobacco-tar latch member 32 is attached to the inner surface of the atomizing sleeve 34, so as to protect the tobacco tar in the tobacco-tar storage chamber 10 easily overflowing along the inner surface of the atomizing sleeve 34, thus further preventing the tobacco tar from leaking to the channel of air flow. Advantageously, the tobacco-tar inlet 341 and the heating wire assembly 31 are respectively arranged on two opposite end portions or two opposite side portions of the tobacco-tar latch member 32, so that the tobacco tar in the tobacco-tar storage chamber 10 should be transmitted to the heating wire assembly 31 through the tobacco-tar latch member 32, thus preventing too much tobacco tar flowing to the heating wire assembly 31, and further protecting the smoker tasting the tobacco tar without timely atomization.

The air pipe 35 is configured of a hollow cylindrical structure, with two openings respectively defined in its two opposite end portions. The air pipe 35 is mounted on an end portion of the internal electrode 332 abutting the tobacco-tar storage chamber 10. In this embodiment, an end portion of the air pipe 35 sheaths an outer surface of an end portion of the internal electrode 332 abutting the tobacco-tar storage chamber 10. The air pipe 35 and the air inlet 3321 communicate with each other, and are coaxial.

The end cover 36 is configured of approximately a hollow cylindrical structure, and mounted on an end portion of the atomizing sleeve 34 far away from the external electrode 331. A through-hole (not labeled) communicating with the air pipe 35 is defined axially in the end cover 36. An end surface of the end cover 36 far away from the atomizing sleeve 34 abuts against the sealing member 6 to ensure smooth circulation of air flow in the atomizer.

As shown in FIG. 5 and FIG. 2, the tobacco-tar blocked pipe 4 is configured of a hollow cylindrical structure, and provided with two openings respectively defined in its two opposite end portions. The tobacco-tar blocked pipe 4 is mounted on a bottom surface in the counterbore portion 131; an inner surface in the counterbore portion 121 and an outer surface of the tobacco-tar blocked pipe 4 cooperatively form the tobacco-tar storage chamber 10 configured for storing the tobacco tar. The electrode assembly 33 seals an end portion of the tobacco-tar storage chamber 10 far away from the suction nozzle 2, that is, the electrode assembly 33 is hermetically mounted in the tobacco-tar filler hole 13 of the tobacco-tar storage chamber 10, to form the hermetical tobacco-tar storage chamber 10 in the sleeve 1. The tobacco tar is stored in the tobacco-tar storage chamber 10, so as to effectively avoid the leakage of the tobacco tar. Advantageously, the tobacco-tar blocked pipe 4 is mounted in the sleeve body 11; and a distance is configured between an end surface of the tobacco-tar blocked pipe 4 far away from the suction nozzle 2 and an end surface of the sleeve body 11 far away from the suction nozzle 2. When the atomizing core 3 is inserted in the tobacco-tar blocked pipe 4, the tobacco-tar inlet 341 in the atomizing sleeve 34 is located between the tobacco-tar blocked pipe 4 and the electrode assembly 33.

As shown in FIG. 5 and FIG. 2, the one-way valve 5 is configured for turning on or cutting off communication between the smoke outlet 21 and the through-hole portion 122. When air flow flows from the through-hole portion 122 to the smoke outlet 21, the one-way valve 5 turns on the communication between the smoke outlet 21 and the through-hole portion 122; when air flow flows from the smoke outlet 21 to the through-hole portion 122, the one-way valve 5 cuts off the communication between the smoke outlet 21 and the through-hole portion 122. The structure of the one-way valve 5 can prevent smoke flowing back to the atomizer or even further flowing into the battery assembly through the atomizer and thus effectively avoid circuits in the battery assembly being damaged by contamination of the tobacco tar. In this embodiment, the one-way valve 5 is a conventional structure in the prior art, which is not further described herein.

As shown in FIG. 5 and FIG. 2, the sealing member 6 is configured for achieving sealing connection between the atomizing core 3 and the one-way valve 5. The sealing member 6 is configured of approximately a hollow cylindrical structure, and provided with good elasticity and sealing performance. The sealing member 6 is resisted between the atomizing core 3 and the one-way valve 5, and communicates with the atomizing core 3 and the one-way valve 5. In this embodiment, the sealing member 6 is resisted between the end cover 36 and the one-way valve 5.

As shown in FIG. 2, the sealing ring 7 is configured for achieving sealing between the connecting member 334 and the sleeve body 11. The sealing ring 7 is provided with good elasticity and sealing performance, and the sealing ring 7 is mounted between an outer surface of the connecting member 334 and an inner surface of the sleeve body 11 to achieve the sealing between the outer surface of the connecting member 334 and the inner surface of the sleeve body 11, to effectively prevent the tobacco tar in the tobacco-tar storage chamber 10 from leaking from a connection point between the connecting member 334 and the sleeve body 11. In this embodiment, two sealing ring 7 are provided, which further improves sealing performance between the atomizing core 3 and the sleeve 1.

An atomizing channel in the atomizer is shown in FIG. 1; the air inlet 3321, the air pipe 35, the end cover 36, the sealing member 6, the one-way valve 5 and the smoke outlet 21 are communicated in sequence. When the atomizing core 3 is in operation, air enters from the air inlet 3321 into the air pipe 35, in which case, smoke generated by the heating wire assembly 31 passes through the air pipe 35, the end cover 36, the sealing member 6, the one-way valve 5 and the smoke outlet 21 in sequence, and is discharged from the smoke outlet 21.

When the atomizer is assembled, mount the one-way valve 5 in the through-hole portion 122 at first, mount the sealing member 6 in the limiting part 14, and make the sealing member 6 abut against the one-way valve 5, and then insert the tobacco-tar blocked pipe 4 into the limiting part 14, and make the tobacco-tar blocked pipe 4 abut against the sealing member 6, aim the atomizing sleeve 34 in the atomizing core 3 at the tobacco-tar blocked pipe 4, and insert the atomizing sleeve 34 into the tobacco-tar blocked pipe 4, and connect the electrode assembly 33 to the tobacco-tar filler hole 13 of the tobacco-tar storage chamber 10 at last.

When implementing the atomizer of the present embodiment, the following advantageous effects can be achieved:

1. The atomizer is provided with a structure that the tobacco-tar inlet 341 and the heating wire assembly 31 are respectively arranged on two opposite end portions of the tobacco-tar latch member 32, and thus the tobacco tar in the tobacco-tar storage chamber 10 should be transmitted to the heating wire assembly 31 through the tobacco-tar latch member 32, in which case, it would not cause overflow of tobacco tar flowing to the heating wire assembly 31, so as to efficiently avoid smoker tasting the tobacco tar without atomization because of the lack of timely atomizing. The tobacco-tar latch member 32 of the present embodiment can have a function of transmitting the tobacco tar, as well as preventing the tobacco tar from permeating into the air pipe 34, so as to prevent a smoker from tasting the tobacco tar without atomization, thus guaranteeing a good user experience.

2. With The atomizer's structure of the one-way valve 5, the smoke can be prevented to flowing back to the atomizer or even flowing into the battery assembly through the atomizer during operation, and thus effectively avoid circuits in the battery assembly being damaged by contamination of the tobacco tar.

3. As the heating wire assembly is mounted on an end portion of the air pipe far away from the electrode assembly, during operation, the distance of the smoke generated by atomizing the tobacco tar flowing out from the smoke outlet 21 is short, and it can avoid a smoker tasting condensed tobacco tar generated effectively, further improving a user comfort level.

4. As the tobacco-tar filler hole 13 is defined in an end portion of the sleeve 1 far away from the suction nozzle 2, when adding or replacing tobacco tar in the atomizer, just the atomizing core 3 would be disassembled from the sleeve 1, the tobacco-tar filler hole 13 be turned up, and the tobacco tar can be injected into the tobacco-tar storage chamber 10 through the tobacco-tar filler hole 13. With this structure, adding or replacing the tobacco tar can be convenient. Compared with adding or replacing the tobacco tar through an end portion of the suction nozzle 2 in prior art, the method of adding or replacing the tobacco tar of the present disclosure can avoid contaminating the suction nozzle 2, and thus the use health level of the atomizer can be improved.

5. The atomizing core 3 is detachably mounted on the sleeve 1 and replaceable so that maintenance cost of the atomizer can be reduced.

Figure 6:
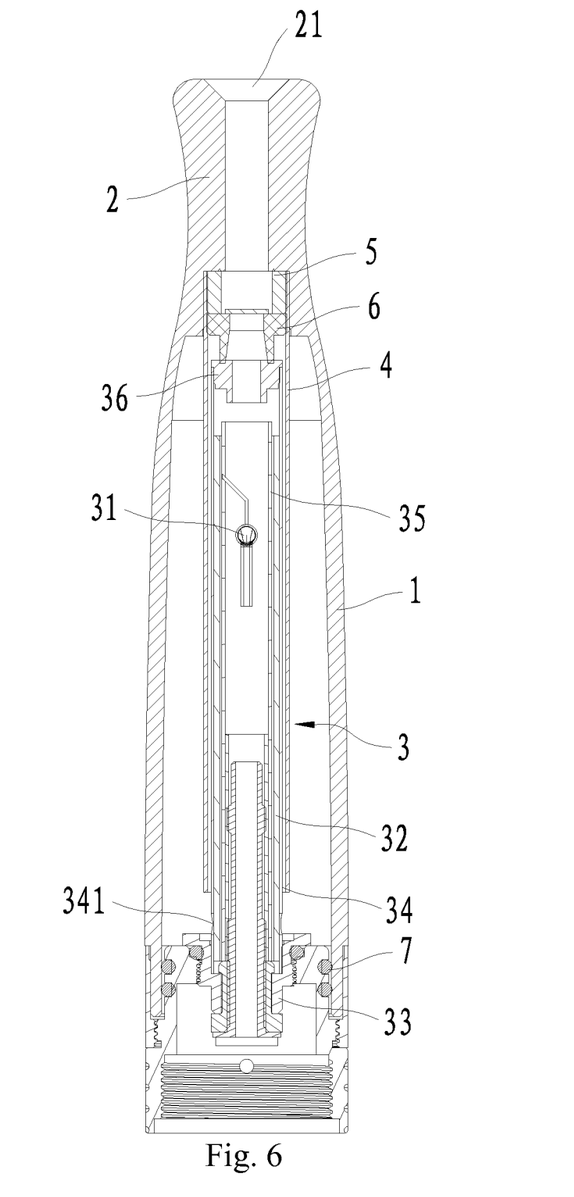
FIG. 6 is an inner structural schematic view of an atomizer of a second preferred embodiment of the present disclosure.

As shown in FIG. 6, according to a second preferred embodiment of the present disclosure, an atomizer is provided, and the difference between the first preferred embodiment and the second preferred embodiment lies in an assembly structure of the tobacco-tar blocked pipe 4, the one-way valve 5 and the sealing member 6. In this embodiment, the tobacco-tar blocked pipe 4 is mounted on an outer surface of the one-way valve 5, and the one-way valve 5 is located in an end portion of the tobacco-tar blocked pipe 4 abutting the suction nozzle 2. During the assembly of the atomizer, firstly the sealing member 6 should be mounted in the tobacco-tar blocked pipe 4, then the one-way valve 5 should be arranged in the tobacco-tar blocked pipe 4, and abut against the sealing member 6, and finally the tobacco-tar blocked pipe 4 would be inserted into the limiting part 14, in which case, the assembly of the tobacco-tar blocked pipe 4, the one-way valve 5 and the sealing member 6 is accomplished. The assembly is convenient to operate, and can improve assembly efficiency of the atomizer.

Based on the structure of the aforementioned atomizer, the present disclosure further provides an electronic cigarette, and the electronic cigarette comprises the atomizer described in the embodiments and a battery assembly detachably connected to the atomizer. The electronic cigarette has the same advantageous effects of the embodiments.

While the embodiments of the present disclosure are described with reference to the accompanying drawings above, the present disclosure is not limited to the abovementioned specific implementations. In fact, the abovementioned specific implementations are intended to be exemplary not to be limiting. In the inspiration of the present disclosure, those ordinary skills in the art can also make many modifications without breaking away from the subject of the present disclosure and the protection scope of the claims. All these modifications will be included within the scope of the appended claims.

What is claimed is:

1. An atomizer, configured for assembling with a battery assembly to form an electronic cigarette, the atomizer comprising a sleeve and an atomizing core, with a suction nozzle formed on an end portion of the sleeve, and a smoke outlet defined in an end portion of the suction nozzle, wherein, a tobacco-tar storage chamber configured for accommodating tobacco tar and an accommodating chamber configured for accommodating the atomizing core are defined in the sleeve; an end portion of the sleeve far away from the suction nozzle is configured as an opening end; a tobacco-tar filler hole communicating with the tobacco-tar storage chamber and the accommodating chamber is defined in the opening end; the atomizing core is detachably mounted in the sleeve and completely fits to seal the tobacco-tar filler hole;
    the atomizing core includes an atomizing sleeve inserted in the accommodating chamber, an electrode assembly inserted into an end portion of the atomizing sleeve and configured for electrically connecting with the battery assembly, a heating wire assembly accommodated in the atomizing sleeve and electrically connecting with the electrode assembly, and a tobacco-tar storage member made of oil absorption material and configured for transmitting the tobacco tar to the heating wire assembly to atomize; a tobacco-tar inlet communicating with the tobacco-tar storage chamber is defined in an end portion of the atomizing sleeve far away from the suction nozzle; the tobacco-tar storage member is sheathed in the atomizing sleeve; the tobacco-tar inlet and the heating wire assembly are respectively arranged on two opposite side portions of the tobacco-tar storage member;
    the sleeve includes a sleeve body and a stepped hole defined in the sleeve body; the stepped hole includes a counterbore portion and a through-hole portion communicating with the smoke outlet; the atomizer further comprises a hollow tobacco-tar blocked pipe mounted on a bottom surface in the counterbore portion; an inner surface in the counterbore portion and an outer surface of the tobacco-tar blocked pipe cooperatively form the tobacco-tar storage chamber; an inner surface of the tobacco-tar blocked pipe forms the accommodating chamber.

2. The atomizer according to claim 1, wherein, the electrode assembly includes an external electrode and an internal electrode, and the external electrode and the internal electrode are respectively configured for electrically connecting with the battery assembly; an outer portion of the internal electrode is sheathed in the external electrode; the atomizing sleeve is inserted in the external electrode; a hollow air pipe is connected to an end portion of the internal electrode; the heating wire assembly is mounted in the air pipe; the tobacco-tar storage member is rested between the atomizing sleeve and the air pipe; two opposite mounting holes are defined in the lateral surface of the air pipe; two terminals of the heating wire assembly are respectively mounted in the two mounting holes;
    an air inlet communicating with an outside of the atomizer is defined in the internal electrode; the air inlet, the air pipe and the smoke outlet are connected in sequence.

3. The atomizer according to claim 1, wherein, the tobacco-tar storage member is a cotton pipe coaxial with the atomizing sleeve; an outer surface of the wool pipe abuts against an inner surface of the atomizing sleeve.

4. The atomizer according to claim 1, wherein the atomizer further comprises a one-way valve configured for turning on or cutting off communication between the smoke outlet and the through-hole portion; when air flow flows from the through-hole portion to the smoke outlet, the one-way valve turns on the communication between the smoke outlet and the through-hole portion; when air flow flows from the smoke outlet to the through-hole portion, the one-way valve cuts off the communication between the smoke outlet and the through-hole portion.

5. The atomizer according to claim 4, wherein the one-way valve is mounted in the through-hole portion; an outer surface of the one-way valve is sheathed in the tobacco-tar blocked pipe.

6. The atomizer according to claim 1, wherein the sleeve is integrated with the suction nozzle; a diameter of the suction nozzle opposite to the sleeve is reduced, the suction nozzle is provided with an arc structure, and the suction nozzle is made of soft plastic material or wood material.

7. The atomizer according to claim 1, wherein a sealing ring is mounted between the electrode assembly and the tobacco-tar filler hole.

8. The atomizer according to claim 1, wherein the counterbore portion is defined at an end of the sleeve, the end of the sleeve is close to the suction nozzle, and a bottom surface in the counterbore portion extends towards a side far away from the suction nozzle to form a limiting part; an end portion of the tobacco-tar blocked pipe is inserted in the limiting part.

9. The atomizer according to claim 4, wherein the atomizer further comprises a sealing member is hermetically mounted between the atomizing core and the one-way valve.

10. The atomizer according to claim 1, wherein the electrode assembly comprises the electrode assembly includes an external electrode, an internal electrode, an insulating member and a connecting member;

a first external thread is defined on the outer surface of the connecting member, correspondingly, a first internal thread corresponding to the first external thread is defined on an inner surface of an end portion of the sleeve body far away from the suction nozzle, and the atomizing core is detachably mounted on the sleeve through the first external thread of the connecting member.

11. An electronic cigarette comprising an atomizer and a battery assembly connecting with the atomizer; the atomizer comprising a sleeve and an atomizing core, with a suction nozzle formed on an end portion of the sleeve, and a smoke outlet defined in an end portion of the suction nozzle, wherein, a tobacco-tar storage chamber configured for accommodating tobacco tar and an accommodating chamber configured for accommodating the atomizing core are defined in the sleeve; an end portion of the sleeve far away from the suction nozzle is configured as an opening end; a tobacco-tar filler hole communicating with the tobacco-tar storage chamber and the accommodating chamber is defined in the opening end; the atomizing core is detachably mounted in the sleeve and completely fit to seal the tobacco-tar filler hole;

the atomizing core includes an atomizing sleeve inserted in the accommodating chamber, an electrode assembly inserted into an end portion of the atomizing sleeve and configured for electrically connecting with the battery assembly, a heating wire assembly accommodated in the atomizing sleeve and electrically connecting with the electrode assembly, and a tobacco-tar storage member made of oil absorption material and configured for transmitting the tobacco tar to the heating wire assembly configured to atomize; a tobacco-tar inlet communicating with the tobacco-tar storage chamber is defined in an end portion of the atomizing sleeve far away from the suction nozzle; the tobacco-tar storage member is sheathed in the atomizing sleeve; the tobacco-tar inlet and the heating wire assembly are respectively arranged on two opposite side portions of the tobacco-tar storage member;

the sleeve includes a sleeve body and a stepped hole defined in the sleeve body; the stepped hole includes a counterbore portion and a through-hole portion communicating with the smoke outlet; the atomizer further comprises a hollow tobacco-tar blocked pipe mounted on a bottom surface in the counterbore portion; an inner surface in the counterbore portion and an outer surface of the tobacco-tar blocked pipe cooperatively form the tobacco-tar storage chamber; an inner surface of the tobacco-tar blocked pipe forms the accommodating chamber.

12. The electronic cigarette according to claim 11, wherein the electrode assembly includes an external electrode and an internal electrode, and the external electrode and the internal electrode are respectively configured for electrically connecting with the battery assembly; an outer portion of the internal electrode is sheathed in the external electrode; the atomizing sleeve is inserted in the external electrode; a hollow air pipe is connected to an end portion of the internal electrode; the heating wire assembly is mounted in the air pipe; the tobacco-tar member is rested between the atomizing sleeve and the air pipe; two opposite mounting holes are defined in the lateral surface of the air pipe; two terminals of the heating wire assembly are respectively mounted in the two mounting holes;

an air inlet communicating with an outside of the atomizer is defined in the internal electrode; the air inlet, the air pipe and the smoke outlet are connected in sequence.

13. The electronic cigarette according to claim 11, wherein the tobacco-tar storage member is a wool pipe coaxial with the atomizing sleeve; an outer surface of the cotton pipe abuts against an inner surface of the atomizing sleeve.

14. The electronic cigarette according to claim 11, wherein the atomizer further comprises a one-way valve configured for turning on or cutting off communication between the smoke outlet and the through-hole portion; when air flow flows from the through-hole portion to the smoke outlet, the one-way valve turns on the communication between the smoke outlet and the through-hole portion; when air flow flows from the smoke outlet to the through-hole portion, the one-way valve cuts off the communication between the smoke outlet and the through-hole portion.

15. The electronic cigarette according to claim 14, wherein the one-way valve is mounted in the through-hole portion; the tobacco-tar blocked pipe is mounted on an outer surface of the one-way valve.

16. The electronic cigarette according to claim 11, wherein a sealing ring is mounted between the electrode assembly and the tobacco-tar filler hole.

17. The electronic cigarette according to claim 11, wherein the counterbore portion is defined at an end of the sleeve, the end of the sleeve is close to the suction nozzle, and a bottom surface in the counterbore portion extends towards a side far away from the suction nozzle to form a limiting part; an end portion of the tobacco-tar blocked pipe is inserted in the limiting part.

18. The electronic cigarette according to claim 14, wherein the atomizer further comprises a sealing member is hermetically mounted between the atomizing core and the one-way valve.

* * * * *